(12) United States Patent
Kojima

(10) Patent No.: US 8,471,392 B2
(45) Date of Patent: Jun. 25, 2013

(54) SEMICONDUCTOR APPARATUS AND ENDOSCOPE APPARATUS

(75) Inventor: Kazuaki Kojima, Suwa (JP)

(73) Assignee: Olympus Corporation, Tokyo (JP)

( * ) Notice: Subject to any disclaimer, the term of this patent is extended or adjusted under 35 U.S.C. 154(b) by 377 days.

(21) Appl. No.: 13/024,373

(22) Filed: Feb. 10, 2011

(65) Prior Publication Data

US 2011/0199473 A1    Aug. 18, 2011

(30) Foreign Application Priority Data

Feb. 15, 2010   (JP) .................................. 2010-030437

(51) Int. Cl.
*H01L 23/495*   (2006.01)

(52) U.S. Cl.
USPC .... 257/783; 257/782; 257/668; 257/E23.036; 348/76

(58) Field of Classification Search
USPC ............. 257/782, 783, 668, E23.036; 348/76
See application file for complete search history.

(56) References Cited

U.S. PATENT DOCUMENTS

| | | | |
|---|---|---|---|
| 4,717,345 A * | 1/1988 | Gordon et al. .................. | 439/67 |
| 6,028,365 A * | 2/2000 | Akram et al. ................. | 257/778 |
| 7,176,568 B2 * | 2/2007 | Urushido ....................... | 257/735 |
| 7,348,492 B1 * | 3/2008 | Kawai et al. ................... | 174/254 |
| 7,417,292 B2 * | 8/2008 | Weigert ......................... | 257/433 |
| 7,592,681 B2 * | 9/2009 | Nakayama ..................... | 257/459 |
| 7,663,223 B2 * | 2/2010 | Pohl .............................. | 257/696 |
| 2008/0137317 A1 * | 6/2008 | Worl et al. ..................... | 361/776 |
| 2009/0047806 A1 * | 2/2009 | Azuma et al. .................. | 439/67 |

FOREIGN PATENT DOCUMENTS

| | | |
|---|---|---|
| JP | 2008-270650 | 11/2008 |
| JP | 2009-158862 | 7/2009 |

\* cited by examiner

*Primary Examiner* — Victor A Mandala
(74) *Attorney, Agent, or Firm* — Scully, Scott, Murphy & Presser, P.C.

(57) ABSTRACT

An image pickup apparatus according to an embodiment includes: an image pickup device chip including an image pickup device formed on a first principal surface thereof and an external terminal for the image pickup device formed on a second principal surface thereof; a wiring board including a distal end portion including a connection pad, a flexure portion flexed at an angle of no less than 90 degrees, and an extending portion, the wiring board including a wiring layer extending from the distal end portion to the extending portion via the flexure portion, the wiring board being kept within a space immediately above the second principal surface of the image pickup device chip; a bonding layer that joins the second principal surface of the image pickup device chip and the distal end portion of the wiring board; and a bonding wire that electrically connects the external terminal and the connection pad.

11 Claims, 6 Drawing Sheets

SEMICONDUCTOR APPARATUS AND ENDOSCOPE APPARATUS

This application claims the benefit of Japanese Application No. 2010-030437 filed in Japan on Feb. 15, 2010, the contents of which are incorporated herein by this reference.

BACKGROUND OF THE INVENTION

1. Field of the Invention

The present invention relates to a semiconductor apparatus including a chip-size packaged semiconductor chip, and an endoscope apparatus including the semiconductor apparatus, and specifically relates to a semiconductor apparatus with a wiring board joined to a second principal surface thereof, the second principal surface opposing a first principal surface with a semiconductor device formed thereon, and an endoscope apparatus including the semiconductor apparatus.

2. Description of the Related Art

A semiconductor apparatus includes a semiconductor chip with a semiconductor device formed thereon, and a package that connects the semiconductor chip to, e.g., an external wiring board. In recent years, in response to the demand for high-density packaging, there has been an increase in use of chip-size packaging (CSP), which enables packaging in a size substantially equal to that of the semiconductor chip.

In CSP, an external connection electrode portion for a semiconductor device is formed on a second principal surface of a semiconductor chip from a first principal surface on which the semiconductor device is formed via through wires. For example, Japanese Patent Application Laid-Open Publication No. 2008-270650 discloses a semiconductor apparatus with stud bumps formed in an electrode portion. However, in the semiconductor apparatus with the above structure, a semiconductor apparatus is mounted on a wiring board via stud bumps by pressure bonding, and thus, stress is applied to the semiconductor chip.

BRIEF SUMMARY OF THE INVENTION

A semiconductor apparatus according to an aspect of the present invention includes: a semiconductor chip including a semiconductor device formed on a first principal surface thereof and an external terminal for the semiconductor device, the external terminal being formed on a second principal surface thereof; a wiring board including a distal end portion including a connection pad, a flexure portion flexed at an angle of no less than 90 degrees, and an extending portion, the wiring board including a wiring layer extending from the distal end portion to the extending portion via the flexure portion, the wiring board being kept within a space immediately above the second principal surface of the semiconductor chip; a bonding layer that joins the second principal surface of the semiconductor chip and the distal end portion of the wiring board; and a bonding wire that electrically connects the external terminal and the connection pad.

An endoscope apparatus according to another aspect of the present invention includes: an image pickup device chip disposed in a distal end portion of an insertion portion thereof, the image pickup device chip including an image pickup device formed on a first principal surface thereof and an external terminal for the image pickup device, the external terminal being formed on a second principal surface thereof; a wiring board including a distal end portion including a connection pad, a flexure portion flexed at an angle of no less than 90 degrees, and an extending portion, the wiring board including a wiring layer extending from the distal end portion to the extending portion via the flexure portion, the wiring board being kept within a space immediately above the second principal surface of the image pickup device chip; a bonding layer that joins the second principal surface of the image pickup device chip and the distal end portion of the wiring board; a bonding wire that electrically connects the external terminal and the connection pad; and a transparent substrate joined to the first principal surface.

DETAILED DESCRIPTION OF THE PREFERRED EMBODIMENTS

<First Embodiment>

Figure 1:
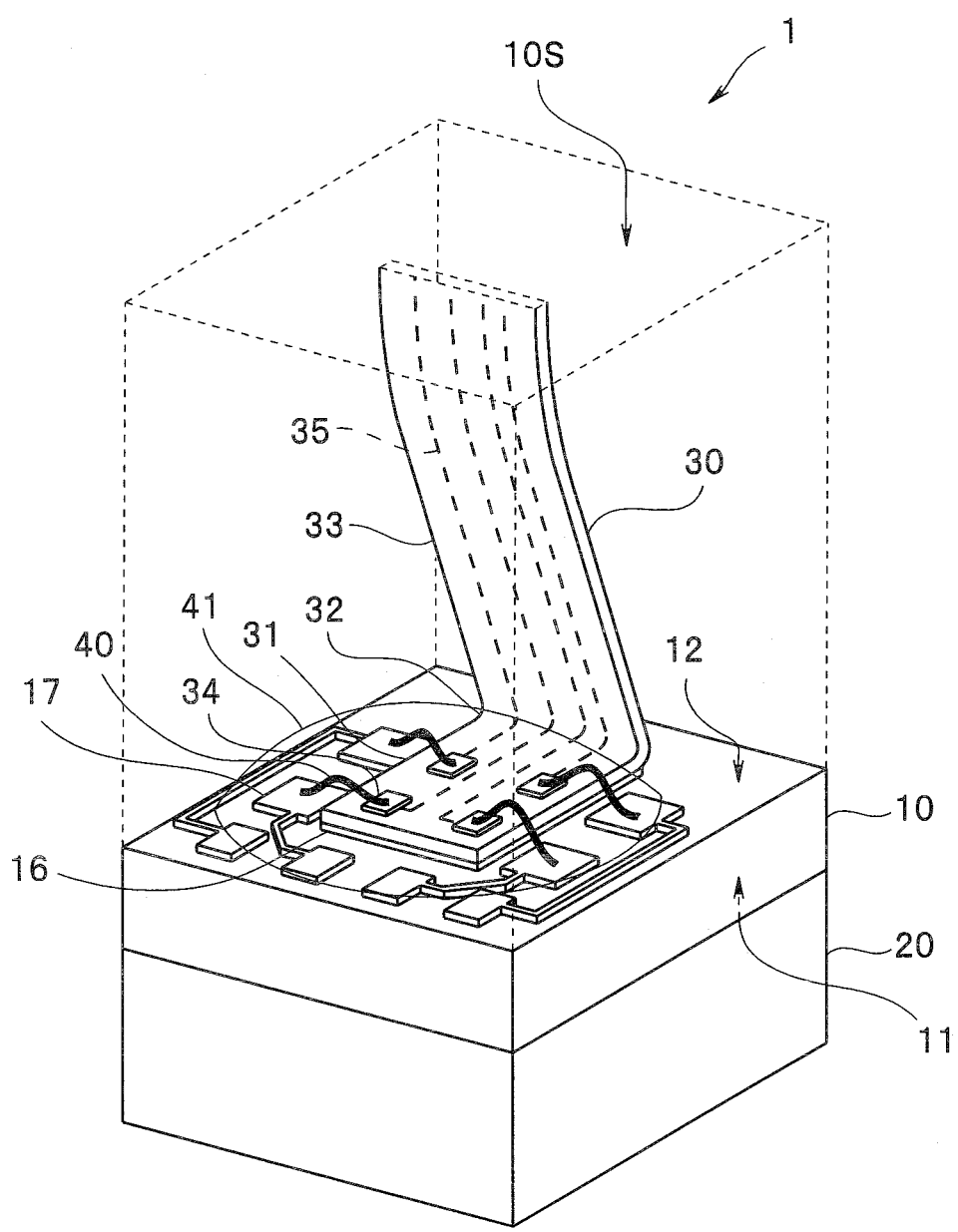
FIG. 1 is a perspective view of an image pickup apparatus according to a first embodiment.
Figure 2A:
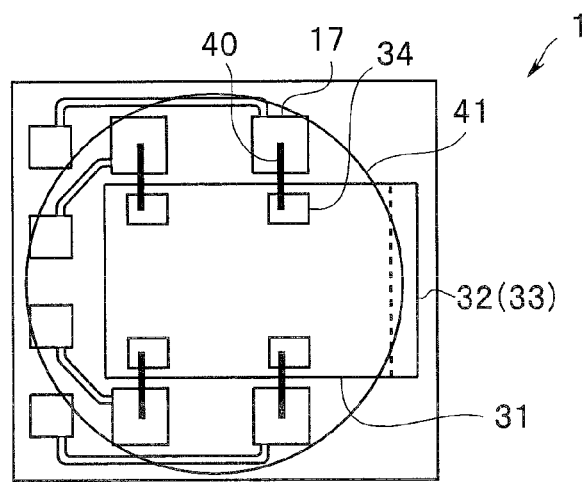
FIG. 2A is a diagram illustrating a top view of the image pickup apparatus according to the first embodiment.
Figure 2B:
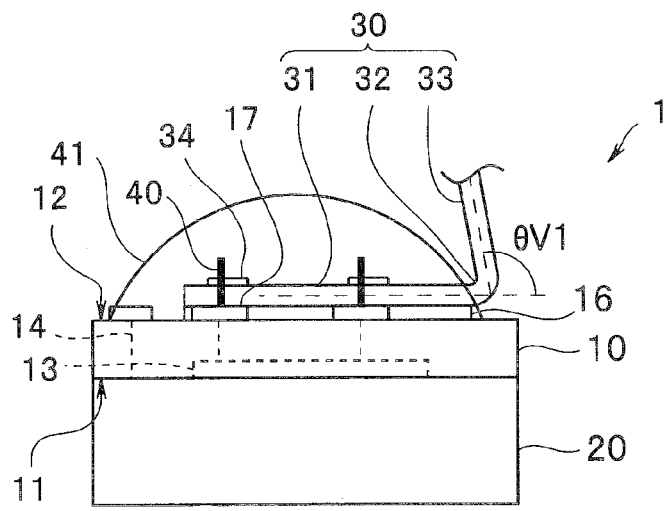
FIG. 2B is a diagram illustrating a side view of the image pickup apparatus according to the first embodiment.
Figure 2C:
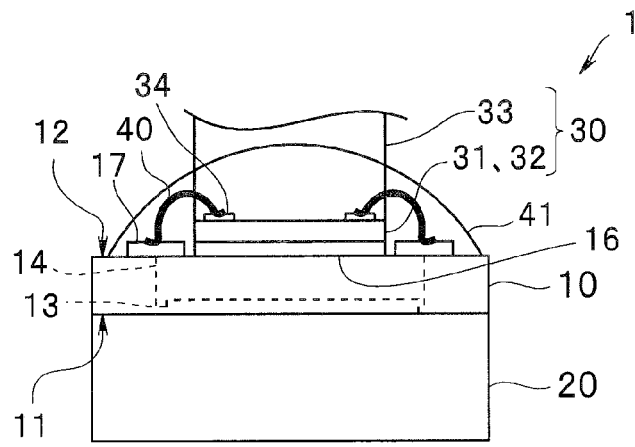
FIG. 2C is a diagram illustrating a front view of the image pickup apparatus according to the first embodiment.

A semiconductor apparatus according to the present embodiment is, for example, an image pickup apparatus 1 disposed in a distal end portion of an endoscope. As illustrated in FIGS. 1 and 2A to 2C, the image pickup apparatus 1 includes a device chip 10, which is a semiconductor chip, a glass substrate 20, which is a transparent substrate joined to a first principal surface 11 of the device chip 10, and a wiring board 30 joined to a center portion of a second principal surface 12 of the device chip 10 via a bonding layer 16.

On the first principal surface 11 of the device chip 10, a solid image pickup device 13 (see FIG. 2B), which is a semiconductor device, is formed. External terminals 17 for signal transmission from/to the solid image pickup device 13, which are formed on the second principal surface 12, are connected to the solid image pickup device 13 via through wires 14 (see FIG. 2B). Although parts on the second principal surface 12 side of the through wires 14 are connected to the respective external terminals 17 by lead wires, the area of the second principal surface 12 other than the area on which the external terminals 17 are formed is covered by an insulating layer (not illustrated). Also, the solid image pickup device may be, e.g., a CCD or CMOS sensor, or a back-illuminated image pickup device. The semiconductor device is not specifically limited to an image pickup device.

The wiring board 30 is a flexible wiring board using a flexible resin of, e.g., polyimide as a base material and including a wiring layer 35 including, e.g., copper. Although for ease of description, the wiring board 30 is expressed below by dividing the wiring board 30 into a distal end portion 31, a flexure portion 32 and an extending portion 33, as illustrated in FIG. 1, the wiring board 30 is a single wiring board, and the boundaries between the divisions are not clearly defined: a joining portion of the wiring board 30 joined to the bonding layer 16 is the distal end portion 31 and the flexed portion of the wiring board 30 is the flexure portion 32. The wiring board only needs to be a flexible wiring board in which at least the flexure portion 32 has flexibility, and the distal end portion 31 and the extending portion 33 may be formed by a rigid wiring board. In the case of a composite wiring board including a flexible wiring board and rigid wiring boards, the boundaries between the divisions are clear.

Connection pads 34 are formed on the distal end portion 31 of the wiring board 30, connection pad 36 (see FIG. 3) is formed on the rear end side of the extending portion 33, and the connection pads 34 and the connection pads 36 are electrically connected via the wiring layer 35. Also, an electric circuit may be formed on the wiring board 30 by connecting an electronic component 56 (see FIG. 3), such as a chip capacitor, to the wiring layer 35 via a connection pad (not illustrated).

The distal end portion 31 of the wiring board 30 is joined to the second principal surface 12 of the device chip 10 via the bonding layer 16. Furthermore, the external terminals 17 for the solid image pickup device 13 and the connection pads 34 on the wiring board 30 are connected by bonding wires 40. Stress exerted between the terminals connected by the bonding wires 40 is extremely small. Also, the effect of heat and stress exerted during wire bonding is not large. The image pickup apparatus 1 illustrated in, e.g., FIG. 1 uses a seal material 41, which includes a resin, to protect the bonding wires 40, which are inferior in mechanical strength, and hold the shape of the flexure portion 32.

Meanwhile, the flexible flexure portion 32 of the wiring board 30 is flexed at an angle ($\theta V1$) of no less than 90 degrees relative to the joining portion joined to the bonding layer 16. Thus, the wiring board 30 including the extending portion 33 is kept within a space 105 immediately above the second principal surface 12 of the device chip 10. Since the extending portion 33 needs to mount the electronic component 56 thereon and/or be connected to a cable, a longitudinal dimension (length) of the extending portion 33 of the wiring board 30 depends on the sizes of the components to be mounted thereon. For example, the longitudinal dimension is twice to eight times the length of a side of a principal surface of the distal end portion 31. The wiring board 30 may be a single-layer wiring board or a multilayer wiring board at least including a wiring layer formed on each of two surfaces thereof.

Next, a method for manufacturing an image pickup apparatus 1 will be described.

First, multiple solid image pickup devices 13 are formed on a front surface (first principal surface 11) of a silicon wafer using a known semiconductor process. Then, a glass wafer of a size that is substantially the same as that of the silicon wafer is joined to the surface of the silicon wafer on which the solid image pickup devices 13 are formed, as a protective material, and a grinding process is performed from the back surface (second principal surface 12) side of the silicon wafer. After the thickness of the silicon wafer has been reduced as a result of the grinding process, e.g., etching is performed from the back surface side, thereby through holes being formed, and the inner portions of the through holes are made to be conductive using, e.g., a conductive paste, and a plating method or a sputtering method, thereby the through wires 14 being formed. Subsequently, the silicon wafer with the glass wafer joined thereto is cut into pieces, thereby the device chip 10, which is an image pickup device chip with the glass substrate 20 joined thereto, being prepared. The wiring board 30 is prepared by sticking, e.g., a copper foil and polyimide, which is a base material, together and then performing etching, or using, e.g., a plating method, and as necessary, the electronic component 56 is mounted on the wiring board 30.

Then, the distal end portion 31 of the wiring board 30 is joined to the center portion of the second principal surface 12 of the device chip 10 via the bonding layer 16. Next, the external terminals 17 for the solid image pickup device 13 and the connection pads 34 on the wiring board 30 are connected using a wire bonding apparatus. The bonding wires 40 are formed by joining metal thin wires, which include, e.g., gold or aluminum, to the external terminals 17 and the connection pads 34 by means of pressure bonding using, e.g., heat generated by ultrasound vibrations.

Then, the flexure portion 32 of the wiring board 30 is largely flexed at the angle ($\theta V1$) of no less than 90 degrees relative to the joining portion joined to the bonding layer 16. The flexion angle of the wiring board 30 before the flexion is 0 degrees. With the flexion angle of no less than 90 degrees, the wiring board 30 can be arranged within the space 10S immediately above the second principal surface 12 of the device chip 10, and the flexion angle is determined according to the length of the extending portion 33 and the sizes and shapes of the components to be mounted on the extending portion 33.

Furthermore, in order to protect the bonding wires 40 and maintain the shape of the flexure portion 32, the seal material 41, which is a seal portion including, e.g., a resin, is disposed on the second principal surface 12. Furthermore, a cable is connected to the connection pads 36 on the extending portion 33 of the wiring board 30 by means of soldering.

The image pickup apparatus 1 according to the present embodiment has been prepared using a chip-size packaging: the external terminals 17 for the solid image pickup device 13 and the connection pads 34 on the wiring board 30 are connected by the bonding wires 40, and the wiring board 30 is flexed and kept within a project area for the device chip 10. Thus, in the image pickup apparatus 1, stress exerted on the solid image pickup device 13, which is a semiconductor device, is small. Accordingly, the solid image pickup device 13 has stable characteristics, and less likely to cause, e.g., noise in image signals. Furthermore, since the wiring board 30 is kept within the space 10S immediately above the second principal surface 12 of the device chip 10, the size in an optical axis direction of the wiring board 30 is small.

Figure 3:
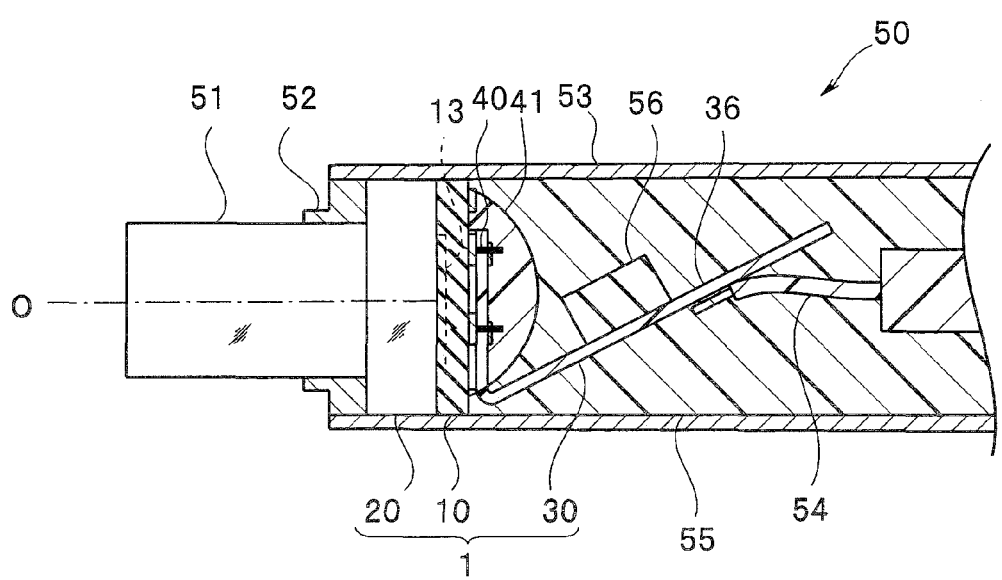
FIG. 3 is a schematic diagram illustrating a cross-sectional structure in which the image pickup apparatus according to the first embodiment is disposed in a distal end portion of an endoscope.
Figure 4:
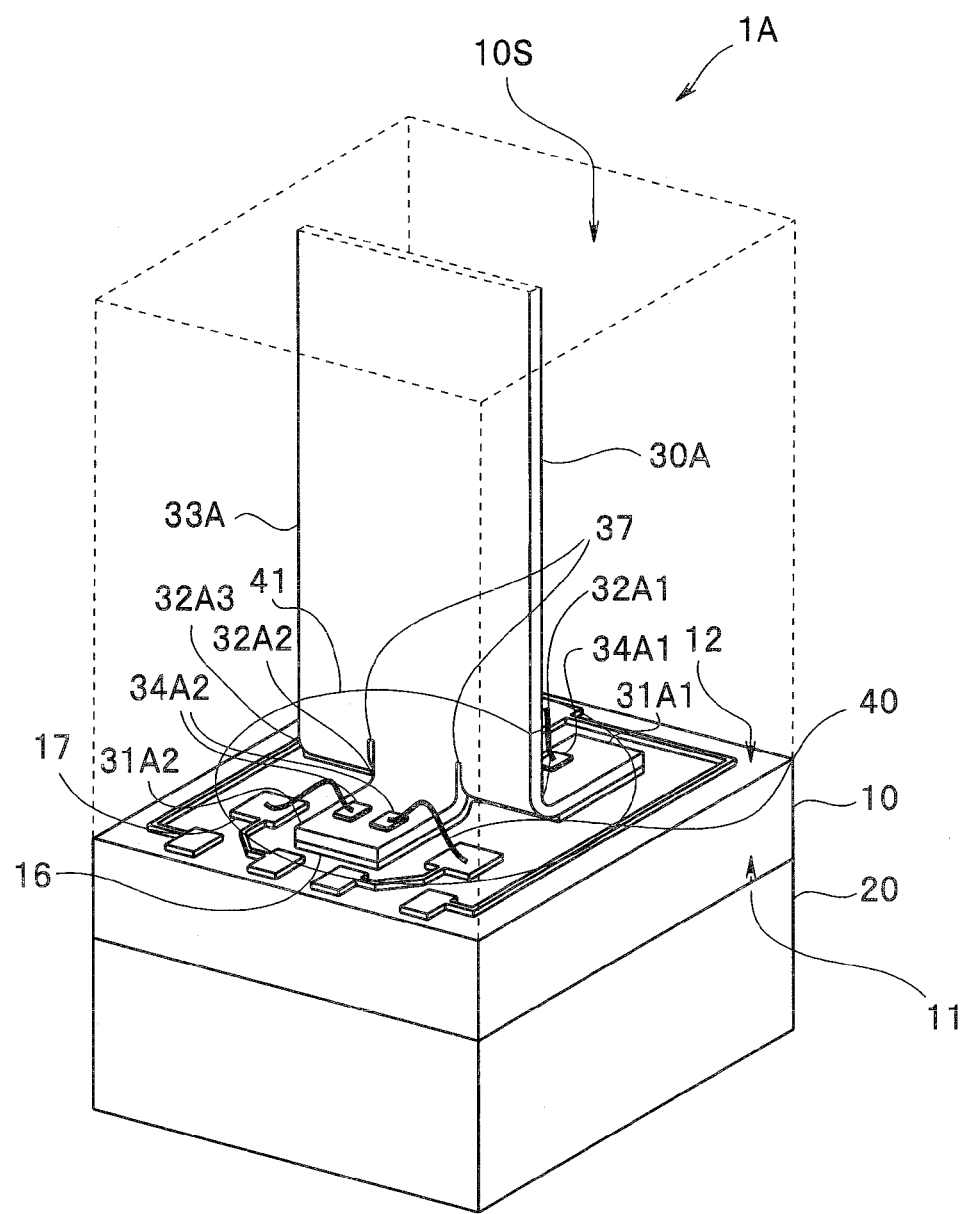
FIG. 4 is a perspective view of an image pickup apparatus according to a second embodiment.

Furthermore, as illustrated in FIG. 3, the image pickup apparatus 1 according to the present embodiment enables reduction of the diameter of a distal end portion of an insertion portion of an endoscope apparatus 50 when the image pickup apparatus 1 is disposed in the distal end portion. An optical system 51 and the image pickup apparatus 1, which are schematically illustrated in FIG. 3, are fixed by a frame portion 52 with an optical axis O as a center. The back side of the image pickup apparatus 1 is covered by a shield frame 53, and an inner portion of the shield frame 53 is charged with a resin filler 55. The electronic component 56, such as a chip capacitor, is mounted on the extending portion 33 of the wiring board 30, and a cable 54 is connected to the connection pads 36.

In other words, the above-described endoscope apparatus 50 includes an image pickup apparatus in a distal end portion of an insertion portion thereof, the image pickup apparatus including: an image pickup device chip including an image pickup device formed on a first principal surface thereof, and external terminals for the image pickup device, which are formed on the second principal surface; a wiring board including connection pads disposed on a distal end portion thereof, and a wiring layer extending from the connection pads to an extending portion thereof; a bonding layer that bonds the distal end portion to the second principal surface; and bonding wires that electrically connect the external terminals and the connection pads, wherein the wiring board includes a flexible flexure portion flexed at an angle of no less than 90 degrees relative to a portion of the wiring board joined to the bonding layer and is kept within a space immediately above the second principal surface of the image pickup device chip.

<Second Embodiment>

Next, an image pickup apparatus 1A according to a second embodiment will be described. Since the image pickup apparatus 1A according to the present embodiment is similar to the image pickup apparatus 1 according to the first embodiment, components that are the same as those of the image pickup apparatus 1 are provided with the same reference numerals as those of the image pickup apparatus 1, and a description thereof will be omitted.

As illustrated in FIGS. 4 and 5A to 5C, a wiring board 30A in the image pickup apparatus 1A according to the present embodiment is a multilayer wiring board at least including a wiring layer on each of two surfaces thereof. A portion from a distal end portion to a portion on the flexure portion side of an extending portion 33A of the wiring board 30A is separated in a width direction into three by two longitudinal slits 37. In other words, the wiring board 30A includes two slits 37 for separating the distal end portion, the flexure portion and the portion on the flexure portion side of the extending portion into three in the width direction. On separated distal end portions 31A1 to 31A3, connection pads 34A1, 34A2 and 34A3 are formed, respectively, although the connection pads 34A1 and 34A3, and the connection pads 34A2 are formed on different surfaces.

Figure 5A:
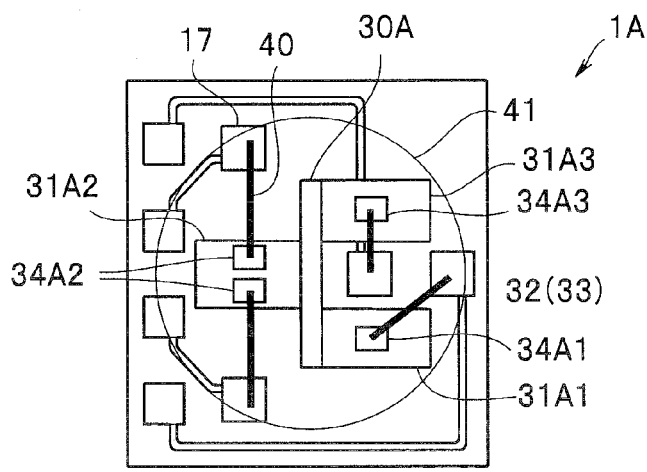
FIG. 5A is a diagram illustrating a top view of the image pickup apparatus according to the second embodiment.
Figure 5B:
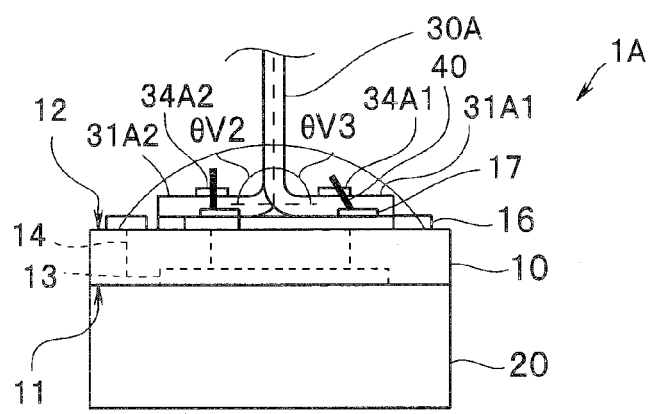
FIG. 5B is a diagram illustrating a side view of the image pickup apparatus according to the second embodiment.
Figure 5C:
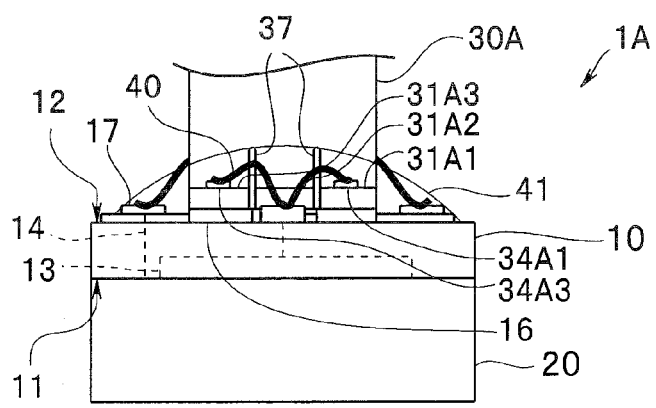
FIG. 5C is a diagram illustrating a front view of the image pickup apparatus according to the second embodiment.

The three separated flexure portion 32A1 to 32A3 are flexed at a right angle alternately in opposite directions so that the respective connection pads are on the upside, and the distal end portions 31A1 to 31A3 are joined to a center portion of a second principal surface 12 of a device chip 10 via a bonding layer 16. In other words, flexion angles θV2 and θV1, which are illustrated in FIG. 5B, are both 90 degrees.

The image pickup apparatus 1A according to the present embodiment enables reduction in stress of the wiring board, which concentrates on the flexure portion, in addition to the advantages provided by the image pickup apparatus 1 according to the first embodiment. Thus, a solid image pickup device 13 has more stable characteristics than those of the image pickup apparatus 1: for example, noise generation is further reduced.

For the image pickup apparatus 1A according to the present embodiment, a case where the three separated distal end portions 31A1 to 31A3 are flexed at a right angle alternately has been described: alternately flexing distal end portions resulting from separating a distal end portion into a plurality of portions enables reduction in stress concentrating on the flexure portion of the wiring board compared to the image pickup apparatus 1.

Figure 6:
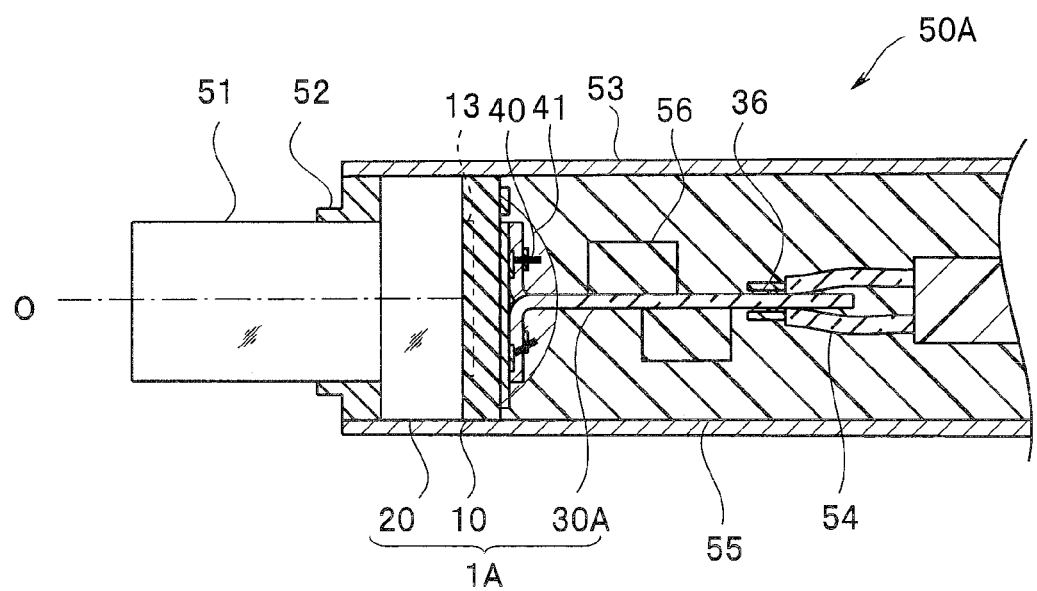
FIG. 6 is a schematic diagram illustrating a cross-sectional structure in which the image pickup apparatus according to the second embodiment is disposed in a distal end portion of an endoscope.

Then, as illustrated in FIG. 6, the image pickup apparatus 1A according to the present embodiment not only enables reduction of the diameter of a distal end portion of an insertion portion of an endoscope apparatus 50A when the image pickup apparatus 1A is disposed in the distal end portion, but also provides a high degree of freedom in arrangement of electronic components 56 to be mounted, and enables a cable 54 to be connected to each of two surface thereof, enabling easy design of the wiring board 30A.

In other words, as illustrated in FIG. 6, in the image pickup apparatus 1A included in the distal end portion of the insertion portion of the endoscope apparatus 50A, the wiring board is a multilayer wiring board, a distal end portion, a flexure portion and a portion of the flexure portion side of an extending portion of the wiring board are separated in a width direction by longitudinal slits, and the plurality of separated flexure portions flexed alternately in opposite directions, in addition to the configuration of the image pickup apparatus 1.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A semiconductor apparatus comprising:
    a semiconductor chip including a semiconductor device formed on a first principal surface thereof and an external terminal for the semiconductor device, the external terminal being formed on a second principal surface thereof;
    a wiring board including a distal end portion including a connection pad, a flexure portion flexed at an angle of no less than 90 degrees, and an extending portion, the wiring board including a wiring layer extending from the distal end portion to the extending portion via the flexure portion, the wiring board being kept within a space immediately above the second principal surface of the semiconductor chip;
    a bonding layer that joins the second principal surface of the semiconductor chip and the distal end portion of the wiring board; and
    a bonding wire that electrically connects the external terminal and the connection pad.

2. The semiconductor apparatus according to claim 1,
    wherein the wiring board is a multilayer wiring board at least including a wiring layer on each of two surfaces thereof, and the distal end portion, the flexure portion and a portion on the flexure portion side of the extending portion are separated in a width direction by longitudinal slits; and
    wherein a plurality of the separated flexure portions are flexed alternately in opposite directions.

3. The semiconductor apparatus according to claim 2, wherein the plurality of flexure portions are flexed at a right angle alternately in opposite directions.

4. The semiconductor apparatus according to claim 1, wherein the distal end portion is bonded to a center portion of the second principal surface of the semiconductor chip.

5. The semiconductor apparatus according to claim 4, further comprising a seal portion that covers the bonding wire and the flexure portion.

6. The semiconductor apparatus according to claim 1,
    wherein the semiconductor device includes an image pickup device; and
    wherein a transparent substrate is joined to the first principal surface.

7. An endoscope apparatus comprising:
an image pickup device chip disposed in a distal end portion of an insertion portion thereof, the image pickup device chip including an image pickup device formed on a first principal surface thereof and an external terminal for the image pickup device, the external terminal being formed on a second principal surface thereof;
a wiring board including a distal end portion including a connection pad, a flexure portion flexed at an angle of no less than 90 degrees, and an extending portion, the wiring board including a wiring layer extending from the distal end portion to the extending portion via the flexure portion, the wiring board being kept within a space immediately above the second principal surface of the image pickup device chip;
a bonding layer that joins the second principal surface of the image pickup device chip and the distal end portion of the wiring board;
a bonding wire that electrically connects the external terminal and the connection pad; and
a transparent substrate joined to the first principal surface.

8. The endoscope apparatus according to claim 7,
wherein the wiring board is a multilayer wiring board at least including a wiring layer on each of two surfaces thereof, and the distal end portion, the flexure portion and a portion on the flexure portion side of the extending portion are separated in a width direction by longitudinal slits; and
wherein a plurality of the separated flexure portions are flexed alternately in opposite directions.

9. The endoscope apparatus according to claim 8, wherein the plurality of flexure portions are flexed at a right angle alternately in opposite directions.

10. The endoscope apparatus according to claim 7, wherein the distal end portion is bonded to a center portion of the second principal surface of the image pickup device chip.

11. The endoscope apparatus according to claim 10, further comprising a seal portion that covers the bonding wire and the flexure portion.

* * * * *